(12) United States Patent
Ruider et al.

(10) Patent No.: US 6,291,715 B1
(45) Date of Patent: Sep. 18, 2001

(54) PROCESS FOR THE PREPARATION OF ALKANOLAMINES HAVING IMPROVED COLOR QUALITY

(75) Inventors: Günther Ruider, Wachenheim; Karl-Heinz Ross, Grünstadt; Boris Breitscheidel, Limburgerhof; Heike Maier; Gerhard Schulz, both of Ludwigshafen; Sylvia Huber, Zwingenberg, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/643,724

(22) Filed: Aug. 23, 2000

(30) Foreign Application Priority Data

Sep. 4, 1999 (DE) ............................................. 199 42 300

(51) Int. Cl.$^7$ .................................................. C07C 209/84
(52) U.S. Cl. ........................ 564/497; 564/498; 564/503; 564/506
(58) Field of Search .................................... 564/497, 498, 564/503, 506

(56) References Cited

U.S. PATENT DOCUMENTS

| 3,207,790 | 9/1965 | Glew . |
| 3,742,059 | * 6/1973 | Dowd ................................. 260/584 R |
| 3,819,710 | 6/1974 | Jordan . |
| 4,567,303 | 1/1986 | Boettger . |
| 5,840,981 | 11/1998 | Fuchs . |
| 5,847,221 | * 12/1998 | Gibson ................................. 564/498 |

FOREIGN PATENT DOCUMENTS

| 2 225 015 | 12/1972 | (DE) . |
| 004 015 | 9/1979 | (EP) . |
| 028 555 | 5/1981 | (EP) . |
| 036 152 | 9/1981 | (EP) . |
| 96/36589 | 11/1996 | (WO) . |

OTHER PUBLICATIONS

Derwent Abst. JO 1160–047, 1989.
J.Apl.Chem.USSR, 61, 1508–9 (1988).
Chem.&Eng.News, Sep. 16, 1996, p. 42.

* cited by examiner

Primary Examiner—Johann Richter
Assistant Examiner—Brian J. Davis
(74) Attorney, Agent, or Firm—Keil & Weinkauf

(57) ABSTRACT

Preparation of alkanolamines having improved color quality by treating the alkanolamine with hydrogen in the presence of a hydrogenation catalyst at elevated temperature, by using, as hydrogenation catalyst, a heterogeneous catalyst comprising Re, Ru, Rh, Pd, Os, Ir, Pt and/or Ag and a support material chosen from the group consisting of activated carbon, alpha-aluminum oxide, zirconium dioxide and titanium dioxide, where the catalyst, in the case of activated carbon as support material, has a cutting hardness of at least 10 N, a side crushing strength of at least 30 N or a compressive strength of at least 25 N.

13 Claims, No Drawings

PROCESS FOR THE PREPARATION OF ALKANOLAMINES HAVING IMPROVED COLOR QUALITY

BACKGROUND OF THE INVENTION

The present invention relates to a process for the preparation of alkanolamines having improved color quality by treating the alkanolamine with hydrogen in the presence of a hydrogenation catalyst at elevated temperature.

Important fields of use of alkanolamines, such as, for example, triethanolamine (TEA), are, for example, soaps, detergents and shampoos in the cosmetics industry, and also dispersants and emulsifiers.

For these and other fields of use, water-clear, colorless alkanolamines having as little discoloration as possible, e.g. measured as APHA color number, which retain these properties even over prolonged storage time (of, for example, 6, 12 or more months) are desired.

It is known that a pure alkanolamine obtained by fractional distillation of an alkanolamine crude product which has, for example, been obtained by reacting ammonia with ethylene oxide or propylene oxide, and initially colorless (color number: about 0 to 20 APHA according to DIN-ISO 6271(=Hazen)), can, after a storage time of from about 4 to 6 weeks, even in a sealed container and with the exclusion of light, gradually turn pale pink or pale yellow and ultimately, particularly if left to stand in light, can turn yellow to brown. This effect is accelerated by the action of higher temperatures. (See e.g.: G. G. Smirnova et al., J. of Applied Chemistry of the USSR 61, p. 1508–9 (1988), and Chemical & Engineering News, Sep. 16, 1996, page 42, middle column.)

The literature describes various processes for the preparation of alkanolamines having improved color quality.

EP-A-4015 describes how mono-, di- and triethanolamine having a lower degree of discoloration are obtained by the addition of phosphorous or hypophosphorous acid or compounds thereof during or following the reaction of ethylene oxide with ammonia and prior to their isolation by distillation.

EP-A-36 152 and EP-A-4015 explain the influence of the materials used in processes for the preparation of alkanolamines on the color quality of the process products and recommend low-nickel or nickel-free steels.

U.S. Pat. No. 3,207,790 describes a process for improving the color quality of alkanolamines by adding a borohydride of an alkali metal to the alkanolamine.

U.S. Pat. No. 3,742,059 and DE-A-22 25 015 describe the improvement in the color quality of alkanolamines by the addition of an alkanolamine ester of boric acid or alkali metal/alkaline earth metal borates.

However, the presence of an auxiliary (stabilizer) for improving the color quality of alkanolamines is undesired in many important application areas.

The earlier German Application No. 19855383.8 dated Jan. 12, 1998 relates to a process for the purification of TEA prepared by reacting aqueous ammonia with ethylene oxide in liquid phase under pressure and at elevated temperature, by separating excess ammonia, water and monoethanolamine from the reaction product, reacting the resulting crude product with ethylene oxide at temperatures from 110 to 180° C., and subsequently rectifying the mixture in the presence of phosphorous or hypophosphorous acid or compounds thereof.

U.S. Pat. No. 3,819,710 discloses a process for improving the color quality of ethanolamines by hydrogenating the crude ethanolamines in the presence of selected catalysts, such as, for example, Pt, Pd, Ru or, preferably, Raney nickel. The process does not lead to ethanolamine products which remain colorless over several months.

According to the invention, it has also been recognized that a general disadvantage when using Raney catalysts is that the reaction product contains undesired traces of aluminum since the alkanolamines act as complexing agents toward aluminum. This leads to permanent damage to the Raney structure and thus to a reduction in the stability and activity of these catalysts.

In addition, according to the invention it has been recognized that if Raney nickel or Raney cobalt are used as catalyst in the purification of alkanolamines, traces of Ni or Co are found in the reaction product since the alkanolamines also act as complexing agents toward nickel and cobalt.

EP-A-28 555 teaches a process for the purification of N,N-dialkylaminoethanols by a catalytic hydrogenation in the heterogeneous phase and subsequent rectification (cf. claim 1 and page 2, lines 23 to 30), where the catalyst comprises a metal chosen from group VIII of the Periodic Table of the Elements, such as, for example, Ni, Co, Pt, Rh or Pd.

JP-A-011 609 47 (Derwent Abstr. No. 89-224471/31, Chem. Abstr. 111:232081r (1989)) describes the purification of dialkylaminoethanol by the steps (a) removal of high-boiling impurities, (b) treatment with hydrogen in the presence of a hydrogenation catalyst which preferably comprises from 0.3 to 7% by weight of a metal from group VIII on a support (such as, for example, Ru/C), and (c) distillation.

According to the invention it has been recognized that many catalyst support materials, such as, for example, gamma-aluminum oxide and magnesium oxide, have the disadvantage that alkanolamines act as complexing agents toward the support material or individual components of the support material, the support material thus leaches out and, as a result, undesired support constituents are found in the reaction product.

BRIEF SUMMARY OF THE INVENTION

It is an object of the present invention to find an alternative, economical, selective and efficient process for the preparation of alkanolamines having improved color quality. The process should allow the discoloration of alkanolamines (such as, for example, triethanolamine and aminoethylethanolamine), e.g. measured as APHA color number, to be reduced, and the color stability to be improved (undesired increase in the color number over the storage period). As a result of the process, no additional substances, such as, for example, stabilizers or traces of metals or other catalyst components, should be introduced into the alkanolamine since these substances, as a result of catalysis of decomposition reactions of the alkanolamine, frequently reduce its color stability, and in the product for certain applications, e.g. in the cosmetics sector, represent a reduction in quality and are undesired. I.e. catalysts used in the process must be leaching-stable. Furthermore, in order for the costs to be as low as possible, it should also be possible to carry out the process at a pressure which is only slightly above atmospheric pressure, or at atmospheric pressure. Finally, the process should permit the use of alkanolamines purified by distillation, where the process product, following removal of the heterogeneous catalyst, is produced in the finished state ("end-of-the-pipe") and no longer requires a further purification step by distillation or rectification since final thermal stressing of the process product by distillation or rectification in most cases leads to deterioration of the color quality.

DETAILED DESCRIPTION OF THE INVENTION

We have found that this object is achieved by a process for the preparation of alkanolamines having improved color quality by treating the alkanolamine with hydrogen in the presence of a hydrogenation catalyst at elevated temperature, which comprises using, as hydrogenation catalyst, a heterogeneous catalyst comprising Re, Ru, Rh, Pd, Os, Ir, Pt and/or Ag and a support material chosen from the group consisting of activated carbon, alpha-aluminum oxide, zirconium dioxide and titanium dioxide, where the catalyst, in the case of activated carbon as support material, has a cutting hardness of at least 10 N, a side crushing strength of at least 30 N or a compressive strength of at least 25 N.

In the process according to the invention, the catalysts are as a general rule preferably used in the form of catalysts which consist only of catalytically active mass and optionally a shaping auxiliary (such as, for example, graphite or stearic acid), if the catalyst is used as a molding, i.e. do not comprise any other catalytically inactive concomitants.

The catalytically active mass can be introduced into the reaction vessel after grinding, as a powder or as granules, or can preferably be introduced into the reactor after grinding, mixing with shaping auxiliaries, shaping and heat-treating, as catalyst moldings—for example as tablets, spheres, rings, extrudates.

The catalytically active mass of the catalyst is defined as the sum of the masses of the catalytically active constituents and of the support materials and essentially comprises one or more noble metals or compounds thereof, such as, for example, oxides, chosen from the group Re, Ru, Rh, Pd, Os, Ir, Pt and Ag, and activated carbon, alpha-aluminum oxide ($\alpha$-$Al_2O_3$), zirconium dioxide ($ZrO_2$), titanium dioxide ($TiO_2$) or mixtures of these support materials.

The sum of the abovementioned catalytically active constituents and of the abovementioned support materials in the catalytically active mass—where the components Re, Ru, Rh, Pd, Os, Ir, Pt and Ag are calculated as metal in oxidation state 0—is customarily from 80 to 100% by weight, preferably from 90 to 100% by weight, particularly preferably from 95 to 100% by weight, in particular greater than 99% by weight, for example 100% by weight.

The catalytically active mass of the catalysts used in the process according to the invention generally comprises
from 50 to 99.95% by weight, preferably from 70 to 99.95% by weight, particularly preferably from 80 to 99.95% by weight, very particularly preferably from 90 to 99.95% by weight, of activated carbon and/or $\alpha$-$Al_2O_3$ and/or $ZrO_2$ and/or $TiO_2$,
from 0.05 to 50% by weight, preferably from 0.05 to 30% by weight, particularly preferably from 0.05 to 20% by weight, very particularly preferably from 0.05 to 10% by weight, of the noble metals Re, Ru, Rh, Pd, Os, Ir, Pt and/or Ag, calculated as metal in oxidation state 0, and
from 0 to 20% by weight, preferably from 0 to 10% by weight, particularly preferably from 0 to 5% by weight, very particularly preferably from 0 to 1% by weight, of one or more elements (oxidation state 0) or inorganic or organic compounds thereof, chosen from the groups I A to VI A and I B to VII B of the Periodic Table of the Elements, and from the group Fe, Co, Ni.

Preferred catalysts comprise in their catalytically active mass from 50 to 99.95% by weight, preferably from 70 to 99.95% by weight, particularly preferably from 80 to 99.95% by weight, very particularly preferably from 90 to 99.95% by weight, of activated carbon and/or $\alpha$-$Al_2O_3$ and from 0.05 to 50% by weight, preferably from 0.05 to 30% by weight, particularly preferably from 0.05 to 20% by weight, very particularly preferably from 0.05 to 10% by weight, of Ru, Rh, Pd and/or Pt, calculated as metal in oxidation state 0.

The catalytically active mass of particularly preferred catalysts consists of from 80 to 99.95% by weight, in particular from 90 to 99.95% by weight, of activated carbon or $\alpha$-$Al_2O_3$ and from 0.05 to 20% by weight, in particular from 0.05 to 10% by weight, of Ru, Rh, Pd and/or Pt, calculated as metal in oxidation state 0.

The catalysts used in the process according to the invention have, in the case of activated carbon as support material, a surface area (according to DIN 66131) of from 500 to 2000 $m^2/g$, preferably from 500 to 1800 $m^2/g$, a pore volume (according to DIN 66134) of from 0.05 to 1.0 $cm^3/g$, preferably from 0.10 to 0.95 $cm^3/g$, and a cutting hardness of at least 10 N (newton), preferably at least 20 N, particularly preferably at least 30 N, or a side crushing strength of at least 30 N, preferably at least 50 N, particularly preferably at least 80 N, or a compressive strength of at least 25 N, preferably at least 40 N, particularly preferably at least 60 N.

The parameter of catalyst hardness or strength is given depending on the shape of the catalyst:

If the catalyst is in the form of granules, the compressive strength is given, in the case of catalyst moldings such as tablets, spheres or rings, the side crushing strength is given, and in the case of catalyst moldings such as extrudates, the cutting hardness is given (cf. Ullmann's Encyclopedia of Industrial Chemistry, 5th, completely revised Ed., Vol. A 5, Chapter 6.3, page 356, 2nd paragraph).

The determination of the parameters of catalyst hardness and strength is explained below.

To prepare the catalysts used in the process according to the invention, various processes are possible.

For example, the catalysts with abovementioned oxidic support material, which consist only of catalytically active mass, are, for example, obtainable by peptizing pulverulent mixtures of the hydroxides, carbonates, oxides and/or other salts of the catalyst components with water, and subsequently extruding and heat-treating the resulting composition.

The catalysts with oxidic support material which consist only of catalytically active mass, used in the process according to the invention, can be prepared using precipitation methods. Thus, for example, they can be obtained by combined precipitation of the metal components from an aqueous salt solution comprising these metals using mineral bases in the presence of a slurry or suspension of finely particulate powder of a sparingly soluble oxygen-containing aluminum, titanium and/or zirconium compound, and subsequently washing, drying and calcining the resulting precipitate. Examples of sparingly soluble, oxygen-containing aluminum, titanium and zirconium compounds which can be used are aluminum oxide, titanium dioxide and zirconium dioxide.

The catalysts having oxidic support material which consist only of catalytically active mass, used in the process according to the invention, are advantageously prepared via a combined precipitation (mixed precipitation) of all of their components. For this purpose, an aqueous mineral base, in particular an alkaline metal base—for example sodium carbonate, sodium hydroxide, potassium carbonate or potassium hydroxide—is expediently added to an aqueous salt solution comprising the catalyst components at elevated temperature and with stirring until precipitation is complete.

The type of salts used is generally not important: since what matters primarily in this procedure is the solubility of the salts in water, a criterion is their good solubility in water, required for the preparation of these relatively strongly concentrated salt solutions. It is considered obvious that in choosing the salts of the individual components, naturally only salts are chosen with anions which do not lead to disturbances, whether by causing undesired precipitations or by impairing or preventing precipitation by complex formation.

Alpha-aluminum oxide can usually not be prepared directly by precipitation, but forms only upon subsequent calcination of the precipitated aluminum oxide (gamma-aluminum oxide) at temperatures of at least 900° C.

The precipitates obtained in these precipitation reactions are generally chemically nonuniform and consist inter alia of mixtures of the oxides, oxide hydrates, hydroxides, carbonates and insoluble and basic salts of the metals used. It may prove favorable for the ability of the precipitates to be filtered if they are aged, i.e. if they are left for some time following precipitation, optionally in warm surroundings or with the passage of air.

The precipitates obtained by these precipitation processes are further processed in the customary manner to give the catalysts according to the invention. Following washing, they are generally dried at from 80 to 200° C., preferably at 100 to 150° C., and then calcined. The calcination is generally carried out at temperatures between 300 and 1100° C., preferably 400 to 600° C., in particular from 450 to 550° C. For the conversion of gamma-aluminum oxide or aluminum oxides of another modification or mixtures thereof into alpha-aluminum oxide, the calcination is carried Out at temperatures of at least 900° C.

Following calcination, the catalyst is expediently conditioned whether by adjusting it to a certain particle size by grinding, or by mixing it, after it has been ground, with shaping auxiliaries, such as graphite or stearic acid, compressing it using a press to give compacts, e.g. tablets, and heat-treating it. The heat-treatment temperatures generally correspond to the temperatures during calcination.

The catalysts prepared in this way comprise the catalytically active metals in the form of a mixture of their oxygen-containing compounds, i.e. in particular as oxides and mixed oxides.

Preferably, the catalysts used in the process according to the invention are prepared by impregnating activated carbon, alpha-aluminum oxide ($\alpha$-$Al_2O_3$), zirconium dioxide ($ZrO_2$), titanium dioxide ($TiO_2$), or mixtures of two or more of these support materials, which are, for example, in the form of powders, granules or moldings, such as extrudates, tablets, spheres or rings.

Zirconium dioxide is, for example, used in the monoclinic or tetragonal form, preferably in the monoclinic form, and titanium dioxide is, for example, used as anatase or rutile.

Activated carbon is generally used with a surface area (according to DIN 66131) of from 500 to 2000 $m^2/g$, preferably from 500 to 1800 $m^2/g$, a pore volume (according to DIN 66134) of from 0.05 to 1.0 $cm^3/g$, preferably from 0.10 to 0.95 $cm^3/g$, and a cutting hardness of at least 10 N, preferably at least 20 N, particularly preferably at least 30 N, or a side crushing strength of at least 30 N, preferably at least 50 N, particularly preferably at least 80 N, or a compressive strength of at least 25 N, preferably at least 40 N, particularly preferably at least 60 N.

The parameters of hardness or strength of the activated carbon support material are given depending on the form of the activated carbon:

If the activated carbon is in the form of granules, the compressive strength is given, in the case of moldings such as tablets, spheres or rings, the side crushing strength is given, and in the case of moldings such as extrudates, the cutting hardness is given (cf. Ullmann's Encyclopedia of Industrial Chemistry, 5th, completely revised Ed., Vol. A 5, Chapter 6.3, page 356, 2nd paragraph).

Examples of such activated carbons are the commercially available grades Norit® RB4 from Norit (The Netherlands), the grades ZGN 3 and ZGN 4 from Mitsubishi (Japan) and the grades Centaur LAD, WS4A AW, WS4A Special and WS4A Supra from Chemviron (Belgium).

The moldings of the abovementioned support materials can be prepared by the customary processes.

These support materials are likewise impregnated by customary processes, as described, for example, in EP-A-599 180, EP-A-673 918 or A. B. Stiles, Catalyst Manufacture—Laboratory and Commercial Preparations, Marcel Dekker, pages 89 to 91, New York (1983), by applying an appropriate metal salt solution in each case in one or more impregnation stages, where the metal salts used are, for example, corresponding nitrates, acetates or chlorides. Following impregnation, the mass is dried and optionally calcined.

The impregnation can be carried out according to the so-called "incipient wetness" method, in which the oxidic support material is, depending on its water absorption capacity, moistened to at most saturation with the impregnation solution. However, the impregnation can also be carried out in supernatant solution.

In multistage impregnation processes, it is advantageous to dry and optionally calcine the support material between individual impregnation steps. It is particularly advantageous to use multistage impregnation when the support material is to be loaded with a relatively large amount of metal.

To apply a plurality of metal components to the support material, the impregnation can be carried out simultaneously with all metal salts or successively in any order of the individual metal salts.

A particular form of impregnation is spray drying, in which the catalyst support mentioned is sprayed in a spray-dryer with the component(s) to be applied in a suitable solvent. An advantage of this variant is the combination of application and drying of the active component(s) in one step.

The catalysts used in the process according to the invention can be reduced before being used. The reduction can be carried out at atmospheric or superatmospheric pressure. If the reduction is carried out at atmospheric pressure, the method involves heating the catalyst under inert gas, for example nitrogen, up to the reducing temperature, and then slowly replacing the inert gas with hydrogen.

For reduction under superatmospheric pressure the procedure in practice involves carrying out the reduction at the pressures and temperatures used subsequently in the process according to the invention. The reduction time is chosen depending on the temperature and hydrogen pressure, i.e. the more drastic the conditions, the shorter the reduction time which can be chosen.

The reduction is generally carried out at a temperature of from 80 to 250° C., a hydrogen pressure of from 0.5 to 350 bar and for a duration of from 1 to 48 h.

It is, however, also possible to use the nonreduced catalysts in the process according to the invention. In this case, the reduction of the respective catalyst then takes place simultaneously under the process conditions. After a short operating time of the process according to the invention of a few hours or a few days, the reduction of the catalyst is usually virtually complete.

Examples of catalysts which can be used in the process according to the invention are supported catalysts as described in WO 96/36589, which comprise from 0.05 to 50% by weight of silver, ruthenium, rhodium, palladium, osmium, iridium, platinum or mixtures thereof and, as support material, activated carbon, α-aluminum oxide, titanium dioxide and/or zirconium dioxide, where the catalyst, in the case of activated carbon as support material, has a cutting hardness of at least 10 N, a side crushing strength of at least 30 N or a compressive strength of at least 25 N.

The alkanolamine used in the process according to the invention, preferably ethanolamine or propanolamine, can be obtained by known processes, e.g. by reacting ammonia or a primary or secondary amine with ethylene oxide or propylene oxide (e.g. as in EP-A-673 920), by the 1,4-addition of ammonia or a primary or secondary amine to an α,β-unsaturated aldehyde (e.g. acrolein) and subsequent reduction (e.g. hydrogenation), by the 1,4-addition of ammonia or a primary or secondary amine to an α,β-unsaturated acid (e.g. acrylic acid) or an α,β-unsaturated ester (e.g. acrylic ester) and subsequent reduction (e.g. hydrogenation), by the 1,4-addition of water to an α,β-unsaturated nitrile (e.g. acrylonitrile) and subsequent reduction (e.g. hydrogenation), amination of corresponding primary or secondary alcohols or aminating hydrogenation of corresponding hydroxyaldehydes or hydroxyketones.

N-(2-aminoethyl)-ethanolamine (AEEA) can be obtained by reacting monoethanolamine or ethylene oxide with ammonia in the presence of hydrogen and a hydrogenating, dehydrogenating or aminating catalyst.

The purity of the alkanolamines used in the process according to the invention, preferably ethanolamines or propanolamines, is generally greater than 70% by weight, in particular greater than 80% by weight. Preference is given to using distilled alkanolamines with a purity of ≧97% by weight, in particular ≧98% by weight, very particularly ≧99% by weight. It is also possible to use mixtures of alkanolamines, in which case the purities given above refer to each alkanolamine of this mixture, or solutions of alkanolamines in an inert solvent, such as, for example, water, alcohols (methanol, ethanol, isopropanol, n-propanol, n-butanol, 2-ethylhexanol), ammonia, ethers (tetrahydrofuran, dioxane), hydrocarbons (toluene, xylene, benzene, pentane, hexane, heptane, mihagol, petroleum ether).

The APHA color number of the alkanolamines used (based on the non-acid-treated alkanolamine) is generally ≦100, in particular ≦50, very particularly ≦20.

The alkanolamines which are preferably used in the process according to the invention are ethanolamines and propanolamines, such as, for example, monoethanolamine (MEA), diethanolamine (DEA), triethanolamine (TEA), aminoethylethanolamine (AEEA), monoisopropanolamine, diisopropanolamine and triisopropanolamine, particularly preferably the ethanolamines TEA and AEEA.

The process according to the invention can be carried out as follows:

The discolored and/or color-unstable alkanolamine is treated in the liquid phase with hydrogen in the presence of the hydrogenation catalyst at elevated temperatures, for example from 70 to 160° C., in particular from 80 to 150° C., very particularly from 100 to 125° C.

The treatment of the alkanolamine with hydrogen can be carried out at atmospheric pressure or superatmospheric pressure, for example at a superatmospheric pressure of from 0 to 50 bar (0 and 5 MPa). Higher pressures are also possible. Preference is given to a superatmospheric pressure of from 0 to 30 bar, in particular from 0 to 20 bar.

In the treatment of the alkanolamine, the hydrogen is generally used in a large molar excess, based on the alkanolamine.

The treatment according to the invention of the alkanolamine with hydrogen in the presence of the hydrogenation catalyst can be carried out either continuously, for example in tubular reactors in downward procedure, upward procedure or circulatory procedure, stirred containers or cascades of stirred containers, or else batchwise, for example in stirred containers. The catalyst is preferably arranged as a fixed bed, although a suspension procedure is also possible.

The required residence time of the alkanolamine over the catalyst arises, inter alia, from the degree of discoloration of the alkanolamine used and from the degree of desired decoloration and/or color stability of the alkanolamine. As a rule, the higher the degree of discoloration of the alkanolamine used in the process according to the invention and the higher the requirements on the color quality of the process product, the longer the time.

Depending on the reaction conditions chosen, residence times of from 10 minutes to a few hours, in particular from 10 minutes to 2 hours, particularly from 20 to 100 minutes, very particularly from 30 to 80 minutes, are generally sufficient.

If the process is carried out continuously, e.g. in a tubular reactor with a fixed catalyst bed, the space velocity is usually from 0.5 to 5 $kg_{alkanolamine}/(l_{cat.} \cdot h)$, preferably from 0.75 to 3 $kg_{alkanolamine}/(l_{cat.} \cdot h)$, particularly preferably from 0.8 to 2 $kg_{alkanolamine}/(l_{cat.} \cdot h)$. The data for the volume of the catalyst refer to the bulk volume.

Following the treatment according to the invention of the alkanolamine with hydrogen in the presence of the heterogeneous catalyst, the catalyst is separated off from the alkanolamine. This can be achieved, for example, by decantation and/or filtration and/or centrifugation. The recovered catalyst can usually be reused in the process.

A significant advantage of the process according to the invention is that the resulting process product is essentially free from impurities which arise from the catalyst used, and thus has virtually the same purity as the alkanolamine used in the process. The prepared alkanolamine generally comprises from 0.1 to 30 ppm, in particular from 0.1 to 20 ppm, very particularly from 0.1 to 10 ppm, of impurities which arise from the catalyst used, such as, for example, Re, Ru, Rh, Pd, Os, Ir, Pt, Ag, Al, Zr, Ti and/or C, and is therefore, in the preferred embodiment, not further worked up by distillation following treatment according to the invention.

The ppm data refer to parts by weight of the elements in oxidation state 0.

The process according to the invention gives an alkanolamine with improved color quality, which, directly after it has been obtained, has an APHA color number of from 0 to 15, in particular from 0 to 10, very particularly from 0 to 5, and which, after acid treatment, which is carried out as described below under D.1) within 0.5 to 1 hour after it has been obtained, has an APHA color number of from 0 to 100, in particular from 0 to 80, very particularly from 0 to 70, and an absolute value for the numerical measure a* according to the CIE-Lab system of from 0 to 3.5 in particular from 0 to 2, very particularly from 0 to 1.7.

The process product, even after a storage period of at least 4 months in a sealed container with the exclusion of light at temperatures of from 10 to 30° C., has, following acid treatment, which is carried out as described below under D.1), an APHA color number of from 0 to 100, in particular from 0 to 80, very particularly from 0 to 70, and an absolute value for the numerical measure a* according to the CIE-Lab system of from 0 to 3.5, in particular from 0 to 3, very particularly from 0 to 2.5.

EXAMPLES

General Preliminary Remarks

A) Determination of the Surface Area, Hardness, Strength and Pore Volume of the Catalysts The pore volume was determined by $N_2$ porosimetry in accordance with DIN 66134.

The surface area was determined in accordance with DIN 66131.

The cutting hardness was determined as follows:

A cutter measuring 0.3 mm in thickness was pressed onto extrudates with increasing force until the extrudate was severed.

The force required is the cutting hardness in N (newton). The determination was carried out on a test device from Zwick, Ulm, with attached rotating plate and freely movable, vertical punch with incorporated cutter measuring 0.3 mm in thickness. The movable punch with the cutter was connected to a load cell for absorbing the force and during the measurement moved toward the attached rotating plate where the extrudate to be measured lay. The test device was controlled by a computer which registered and evaluated the measurement results. From a thoroughly mixed catalyst sample, 25 straight extrudates which were as free from cracks as possible and had an average length of from 2 to 3 times the diameter were taken, the cutting hardnesses of which were determined and then averaged.

The side cutting strength was determined as follows:

Tablets, rings or spheres were subjected to an increasing force between two parallel plates on the convex side until fracture occurred. The force registered upon fracture is the side crushing strength (in the case of spheres also called crushing strength for short). The determination was carried out on a test device from Zwick, Ulm, with attached rotating plate and freely movable, vertical punch which pressed the molding against the attached rotating plate. The freely movable punch was connected to a load cell for absorbing the force. The device was controlled by a computer, which registered and evaluated the measured values. From a thoroughly mixed catalyst sample, 25 perfect (i.e. crack-free and no knocked-off corners) tablets, rings or spheres were taken, the side crushing strength of which was determined and then averaged.

The compressive strength was determined as follows:

To remove moisture, the granules (particle size up to 6 mm) were dried at 120° C. for 2 h prior to measurement. A measured sample of catalyst granules of 20 cm³ was freed from fines on an ASTM 40 mesh (0.42 mm) sieve and weighed into a metal cylinder (3 mm wall thickness, 50 mm height, 27.6 mm internal diameter, cross section 6 cm²) to 0.1 g exactly. The sample was covered with about 50 steel balls (diameter 6 mm) (5 cm³) and, via a spindle, subjected to a weight of 10 kg +/−0.1 kg for 3 min. The contents of the cylinder were then passed over a sieve (ASTSM 40 mesh, 0.42 mm), and the steel balls were removed. The amount of fines was weighed exactly to 1 mg.

Catalyst sample and dust were returned to the cylinder and covered with balls.

The measurement was repeated using a weight of 20, 40, 60, 80 and 100 kg, and each time the fines were weighed.

By plotting a graph, the weight at which 0.5% by weight of fines were produced was determined (interpolation if necessary). The weight in question gave the compressive strength according to the equation weight in kg at 0.5% of fines/cross section of the cylinder in cm².

B) Catalyst Preparations

The Raney nickel used in the Comparative Examples 1, 2 and 4 is commercially available (Degussa, grade: B113 W) and was used in the form of 1.5 mm extrudates and dried prior to use.

The Pd/γ-$Al_2O_3$ catalyst from Comparative Example 3 was prepared as in WO 96/36589 (Catalyst A therein).

The Ru/α-$Al_2O_3$ catalyst of Examples 1, 2 and 32 was prepared as in WO 97/10202 (Example No. 1 therein).

The noble metal/activated carbon catalysts of Examples 3, 8 to 15, 22, 23, 31 and 36 were prepared by impregnation, in a manner which is known industrially per se, of activated carbon moldings (3.5 mm extrudates, Norit® RB4 from Norit), with aqueous solutions of corresponding metal salts (Ru(NO) $(NO_3)_x(OH)_{3-x}$, $Pd(NO_3)_2$, $Pt(NO_3)_2$), drying of the impregnated activated carbon moldings, reduction in a stream of hydrogen (150° C.) and subsequent passivation in a stream of air (120° C.).

The resulting catalysts had a surface area of from 1221 to 1292 m²/g, a pore volume of from 0.13 to 0.46 cm³/g and a cutting strength of 62 N.

The Ru/activated carbon catalyst of Comparative Example 5 was prepared by impregnation, in a manner known industrially per se, of activated carbon of the activated carbon CS type from Jacobi (0.4 to 0.9 mm granules) with an aqueous solution of Ru(NO) $(NO_3)_x(OH)_{3-x}$, drying and reduction in a stream of hydrogen (150° C.) and subsequent passivation in a stream of air (120° C.). The resulting catalyst had a surface area of 1230 m²/g, a pore volume of 0.5 cm³/g and a compressive strength of 4 N.

The catalysts of Examples 4 to 7 and 24 to 27 are rhodium/activated carbon catalysts (extrudates) from Johnson-Matthei (Batch No. 96375) having a surface area of 733 m²/g, a pore volume of 0.36 cm³/g and a cutting strength of 37.5 N.

The catalysts of Examples 16 to 18 and 28 to 30 are rhodium/activated carbon catalysts (1.5 to 2.5 mm extrudates) from Johnson-Matthei (Batch No. 97053) having a surface area of 572 m²/g, a pore volume of 0.29 cm³/g and a compressive strength of 38.2 N.

The catalysts of Examples 19 to 21, 33 and 34 are ruthenium/activated carbon catalysts from Heraeus (extrudates, catalyst number: 97569) having a surface area of 1530 m²/g, a pore volume of 0.80 cm³/g and a compressive strength of 10.6 N.

The catalyst of Example 35 is a ruthenium/activated carbon catalyst from Heraeus (extrudates, catalyst number: 97568) having a surface area of 1673 m²/g, a pore volume of 0.88 cm³/g and a compressive strength of 11.3 N.

C) Apparatuses

To carry out the experiments, two apparatuses were used for the continuous operation, one for experiments under super-atmospheric pressure, and the other for experiments under atmospheric pressure.

C.1) Pressure Apparatus

The feed was metered in via a piston pump and the hydrogen was injected via a control valve to the desired reaction pressure (up to about 45 bar).

The reactor consisted of stainless steel with a double-jacketed tube (oil heating) and had an internal volume of 40 ml which is available for the catalyst filling. The reactor inlet and outlet were blocked with glass balls in order to prevent the catalyst from escaping. In the exit gas of the reactor, the volumetric flow rate was measured, and the stream of exit gas during the treatment was generally adjusted to 5 l of $H_2$/h. The level was maintained via a valve which was controlled via a differential pressure measurement in the separator.

C.2) Atmospheric Pressure Apparatus

The feed was metered in via a piston pump and hydrogen was decompressed to atmospheric pressure via a control valve; the hydrogen flow rate was measured by means of a mass flow rate measurement on the feed side and was adjusted to a value of 5 l of $H_2$/h.

The reactor consisted of glass with a double-jacketed tube (oil heating) and had a heated volume of 70 ml. Glass balls were positioned at both the reactor inlet and outlet, meaning that a volume of about 30 ml remained for the catalyst bed. The reactor product was cooled by means of an air cooler and conveyed to a product vessel.

D) Determination of the Color Quality and Color Stability of the Alkanolamines

To determine the color quality and color stability of the alkanolamines treated, samples were taken from the alkanolamines treated as described below (a) directly following the treatment and (b) following storage at room temperature under atmospheric air in sealed vessels with the exclusion of light according to the storage times given in Table Nos. 1 and 2. These samples were initially subjected to the acid treatment described below in order to intensify the color effects which occur, and then directly, in a spectral color measurement, the values for the numerical measures $a^*$ and $b^*$ according to the CIE-Lab system (according to Judd and Hunter (CIE=Comission International d'Eclairage, Paris); (cf. DIN 6174)) and the APHA value (corresponding to DIN-ISO 6271) were determined. The $a^*$, $b^*$ and APHA values (APHA=Hazen=Pt/Co color number) were determined as per standard in a LICO 200 device from Dr. Lange in a 5 cm cuvette (volume≈20 ml). The $a^*$ value gives the red/green coloration of the sample (a positive $a^*$ value gives the red color content, and a negative $a^*$ value gives the green color content) and the $b^*$ value gives the yellow/blue content (a positive $b^*$ value gives the yellow color content, and a negative $b^*$ value the blue color content). In particular, the desired result is an absolute $a^*$ value which is lower than that in the starting material prior to treatment.

The $a^*$, $b^*$ and APHA values given in Table Nos. 1 and 2 refer in every case to the samples following the acid treatment carried out.

D.1) Acid Treatment of the Alkanolamines

[An acid treatment of an alkanolamine for intensifying color effects was described generally in JP-A-62 019 558 (Derwent Abstract No. 87-067647/10) and JP-A-62 005 939 (Derwent Abstract No. 87-047397/07), according to which TEA is treated (neutralized) with acetic acid, citric acid, sulfuric acid, hydrochloric acid or phosphoric acid.]

Unless stated otherwise, the acid treatment was carried out as follows:

The alkanolamine was mixed with 1000 ppm (parts by weight) of glacial acetic acid and heated at 100° C. for 3 h under nitrogen.

E) Analysis and General

Traces of metals in the alkanolamine following the treatment in the presence of the catalyst were determined by means of atomic absorption spectroscopy. The figures in the tables are in ppm (=mg/kg).

The space velocity is given in the tables in $l_{alkanolamine}/(l_{catalyst} \cdot h)$ The triethanolamine used in the examples had a purity according to GC of $\geqq 99$ area-% and, after the acid treatment described above under D.1), generally had $a^*$ and $b^*$ values between 3 and 4, and the APHA color number was between 30 and 50.

The triethanolamine used in the examples had, without prior acid treatment, an $a^*$ value of 0.2, a $b^*$ value of 1.0 and an APHA color number of 10.

The pressures and temperatures at which each of the examples was carried out are given in Table Nos. 1 and 2.

The results of the treatment of the alkanolamine with hydrogen at a pressure above atmospheric pressure are given in Comparative Examples 1 to 3 and 5, and in Examples 1 to 21 (cf. Table 1).

The results of the treatment of the alkanolamine with hydrogen at atmospheric pressure (AP) are given in Comparative Example 4, and in Examples 22 to 35 (cf. Table 2).

Comparative Examples 1 and 2

30 ml of Raney nickel (1.5 mm extrudates) were dried at 150° C. in a stream of nitrogen (10 l/h). Triethanolamine was treated at the given pressure and the given temperature at a hydrogen flow rate of 5 l of $H_2$/h over the catalyst activated in this way.

Although the treatments in the presence of Raney nickel gave acceptable reduction in the $a^*$ values, the $b^*$ value was, however, sometimes above that of the starting materials.

In addition, the product contained the stated nickel and, in particular, aluminum traces, which is unacceptable.

Comparative Example 3

30 ml of the catalyst having the composition 0.58% by weight of Pd on $\gamma$-$Al_2O_3$ were activated for 16 h at 180° C. under a stream of $H_2$ of 10 l/h. Triethanolamine was treated at the given pressure and at the given temperature at a hydrogen flow rate of 5 l of $H_2$/h over this catalyst activated in this manner.

It was visible even with the naked eye that the reaction product had turned pink, both the $a^*$ and the $b^*$ values had significantly increased and aluminum was leached out.

Comparative Example 4

20 ml of Raney nickel were dried for 3 h at 150° C. under an $H_2$ stream of 5 l/h. Triethanolamine was treated at atmospheric pressure and the stated temperature with a hydrogen stream of 5 l of $H_2$/h over this catalyst activated in this way.

The product contained aluminum and nickel.

Comparative Example 5

33 ml of the catalyst having the composition 1% by weight of Ru on activated carbon were activated for 3 h at 100° C. in a stream of 10 l of $H_2$/h.

The product was still cloudy at 65 operating hours, and the batch was discarded.

Examples 1 and 2

20 ml of the catalyst having the composition 0.05% by weight of Ru on $\alpha$-$Al_2O_3$ support (8×8 mm rings) were activated for 2 h at 100° C. under an $H_2$ stream of 10 l/h. Triethanolamine was treated at the given pressure and the given temperature with a hydrogen stream of 5 l of $H_2$/h over this catalyst activated in this way.

Example 3

30 ml of the catalyst having the composition 1% by weight of Pt. on activated carbon were activated for 2 h at 180° C. under an $H_2$ stream of 10 l/h. Triethanolamine was treated at the given pressure and the given temperature with a hydrogen stream of 5 l of $H_2$/h over this catalyst activated in this manner.

In the run-up phase (14 h) the product was slightly brownish in color, then the product was colorless and water-clear.

Examples 4 to 7

30 ml of the catalyst having the composition 5% by weight of Rh on activated carbon in granule form were activated for 3 h at 100° C. under an $H_2$ stream of 10 l/h. Triethanolamine was treated at the given pressure and the given temperature with a hydrogen stream of 5 l of $H_2$/h over this catalyst activated in this way.

In the run-up phase (14 h) the product was slightly gray in color, then the product was colorless and water-clear.

Examples 8 to 11

Triethanolamine was treated at the given pressure and the given temperature with a hydrogen stream of 5 l of $H_2$/h over 30 ml of the catalyst having the composition 1% by weight of Ru on activated carbon in the form of 3.5 mm extrudates without further activation.

Examples 12 to 15

30 ml of the catalyst having the composition 1% by weight of Pd on activated carbon in the form of 3.5 mm extrudates were activated for 2 h at 100° C. under an $H_2$ stream of 10 l/h. Triethanolamine was treated at the given pressure and the given temperature with a hydrogen stream of 5 l of $H_2$/h over this catalyst activated in this way.

Examples 16 to 18

30 ml of the catalyst having the composition 2% by weight Rh on activated carbon were activated for 2 h at 100° C. under an $H_2$ stream of 10 l/h. Triethanolamine was treated at the given pressure and the given temperature with a hydrogen stream of 5 l of $H_2$/h over this catalyst activated in this way.

Examples 19 to 21

30 ml of the catalyst having the composition 1% by weight of Ru on activated carbon were activated for 2 h at 100° C. under an $H_2$ stream of 10 l/h. Triethanolamine was treated at the given pressure and the given temperature with a hydrogen stream of 5 l of $H_2$/h over this catalyst activated in this way.

Examples 22 to 23

30 ml of the catalyst having the composition as in Example 3 were activated for 2 h at 150° C. under an $H_2$ stream of 5 l/h. Triethanolamine was treated at atmospheric pressure and the given temperature with a hydrogen stream of 5 l of $H_2$/h over this catalyst activated in this way.

In the run-up phase (14 h) the product was slightly brownish in color, but then turned colorless and water-clear.

Examples 24 to 27

30 ml of the catalyst having the composition as in Examples 4 to 7 were activated for 3 h at 100° C. under an $H_2$ stream of 10 l/h. Triethanolamine was treated at atmospheric pressure and the given temperature with a hydrogen stream of 5 l of $H_2$/h over this catalyst activated in this manner.

Examples 28 to 30

30 ml of the catalyst having the composition as in Examples 16 to 18 were activated for 2 h at 100° C. under an $H_2$ stream of 5 l/h. Triethanolamine was treated at atmospheric pressure and the stated temperature with a hydrogen stream of 5 l of $H_2$/h over this catalyst activated in this way.

Example 31

30 ml of the catalyst having the composition as in Examples 8 to 11 were activated for 2 h at 100° C. under an $H_2$ stream of 5 l/h. Triethanolamine was treated at atmospheric pressure and the stated temperature with a hydrogen stream of 5 l of $H_2$/h over this catalyst activated in this way.

Example 32

30 ml of the catalyst as in Examples 1 and 2 were activated for 1.5 h at 100° C. under an $H_2$ stream of 5 l/h. Triethanolamine was treated at atmospheric pressure and the stated temperature with a hydrogen stream of 5 l of $H_2$/h over this catalyst activated in this way.

Examples 33 and 34

30 ml of the catalyst having the composition 1% by weight of Ru on activated carbon (as in Examples 19 to 21) were activated for 2 h at 100° C. under an $H_2$ stream of 5 l/h. Triethanolamine was treated at atmospheric pressure and the given temperature with a hydrogen stream of 5 l of $H_2$/h over this catalyst activated in this way.

Example 35

30 ml of the catalyst having the composition 1% by weight of Ru on activated carbon were activated for 2 h at 100° C. under an $H_2$ stream of 5 l/h. Triethanolamine was treated at atmospheric pressure and the given temperature with a hydrogen stream of 5 l of $H_2$/h over this catalyst activated in this way.

Example 36

Aminoethylethanolamine (AEEA) was treated at 125° C. and a space velocity of 0.5 $l_{AEEA}/l_{catalyst} \cdot h$) with a hydrogen stream of 5 l of $H_2$/h under atmospheric pressure over 50 ml of the catalyst having the composition 1% by weight of Pt on activated carbon in the form of 3 mm extrudates without further activation.

The acid treatment was carried out as follows: AEEA and glacial acetic acid were mixed in the molar ratio of 1:1.5 with cooling and heated for 1 h at 80° C. in a thermostated oil bath.

The Gardner color number (DIN ISO 4630) was measured following the acid treatment with a Dr. Lange, Liquid-Tester LTM1 device.

Following acid treatment, the feed material had a Gardner color number of greater than 8.5 (corresponding to about 8000 to 9000 APHA). The treatment of the AEEA described above reduced the Gardner color number to 4.8 (following acid treatment) (corresponds to about 1200 APHA).

TABLE 1

| Ex. No. # | Pressure [bar] | T [° C.] | Space velocity [1/(1 · h)] | a* value | b* value | APHA | Product [ppm] | Storage time [days] | a* value | b* value | APHA |
|---|---|---|---|---|---|---|---|---|---|---|---|
| Comp. 1 | 45 | 150 | 1.17 | 1.1 | 3.1 | 26 | Al 65 ppm Ni 3 ppm | | | | |
| Comp. 2 | 20 | 150 | 1.17 | 1.1 | 4.0 | 32 | Al 14 ppm Ni <1 ppm | | | | |
| Comp. 3 | 20 | 100 | 1 | 10.4 | 6.7 | 80 | Al 180 ppm Pd <3 ppm | | | | |
| Comp. 5 | 20 | 100 | 1 | | | | cloudy | | | | |
| 1 | 20 | 125 | 1 | −0.3 | 4.4 | 31 | Rh, Al <3 ppm | | | | |
| 2 | 20 | 150 | 1 | −0.4 | 5.4 | 38 | n.d. | | | | |
| 3 | 20 | 150 | 1 | 0.4 | 5.7 | 48 | Pt 2 ppm | | | | |
| 4 | 20 | 100 | 1 | 0.2 | 2.0 | 16 | n.d. | 113 | −0.6 | 7.8 | 59 |
| 5 | 20 | 125 | 1 | 0.1 | 3.3 | 25 | n.d. | 111 | −0.3 | 6.1 | 44 |
| 6 | 20 | 150 | 1 | 0.3 | 2.6 | 20 | Rh <1 ppm | 111 | −0.5 | 7.0 | 50 |
| 7 | 20 | 150 | 3 | 1.6 | 4.0 | 32 | n.d. | | | | |
| 8 | 20 | 100 | 1 | −0.1 | 4.1 | 31 | n.d. | | | | |
| 9 | 20 | 125 | 1 | −0.1 | 7.5 | 59 | Ru <1 ppm | | | | |
| 10 | 20 | 150 | 1 | −0.2 | 7.6 | 58 | n.d. | | | | |
| 11 | 20 | 125 | 3 | 0.4 | 4.4 | 34 | n.d. | | | | |
| 12 | 20 | 100 | 1 | 0.4 | 0 | 1 | n.d. | 104 | 0.3 | 4.5 | 34 |
| 13 | 20 | 125 | 1 | 0.6 | 0.6 | 7 | Pd <3 ppm | 103 | 0.2 | 4.0 | 30 |
| 14 | 20 | 150 | 1 | 0.6 | 0.4 | 5 | n.d. | 100 | 0.9 | 3.1 | 26 |
| 15 | 20 | 150 | 3 | 1.2 | 0.4 | 6 | n.d. | 99 | 2.2 | 3.7 | 33 |
| 16 | 20 | 100 | 1 | 0.8 | 2.1 | 18 | n.d. | 39 | 0.4 | 2.6 | 25 |
| 17 | 20 | 125 | 1 | 0.2 | 1.6 | 12 | n.d. | 39 | 0.3 | 2.3 | 19 |
| 18 | 20 | 150 | 1 | 0.1 | 1.5 | 11 | Rh <3 ppm | | | | |
| 19 | 20 | 100 | 1 | 0.6 | 3.8 | 31 | n.d. | | | | |
| 20 | 20 | 125 | 1 | 0.5 | 2.9 | 23 | n.d. | | | | |
| 21 | 20 | 150 | 1 | 1.2 | 2.6 | 23 | n.d. | | | | | n.d.: not determined

TABLE 2

| Ex. No. # | Pressure [bar] | T [° C.] | Space velocity [1/(1 · h)] | a* value | b* value | APHA | Product [ppm] | Storage time [days] | a* value | b* value | APHA |
|---|---|---|---|---|---|---|---|---|---|---|---|
| Comp. 4 | AP | 125 | 1 | 1.6 | 6.3 | 51 | Ni 8 ppm Al 33 ppm | 121 | 0.5 | 30.3 | 246 |
| 22 | AP | 150 | 1 | 0.8 | 3.7 | 31 | Pt <3 ppm | | | | |
| 23 | AP | 150 | 2 | 1.5 | 3.9 | 34 | n.d. | | | | |
| 24 | AP | 100 | 1 | −0.2 | 4.5 | 35 | n.d. | | | | |
| 25 | AP | 125 | 1 | −0.2 | 5.7 | 42 | n.d. | | | | |
| 26 | AP | 150 | 1 | −0.3 | 4.1 | 30 | Rh <1 ppm | | | | |
| 27 | AP | 150 | 2 | 0.5 | 4.1 | 31 | n.d. | | | | |
| 28 | AP | 100 | 1 | −0.3 | 4.7 | 35 | n.d. | 49 | 0.8 | 6.6 | 54 |
| 29 | AP | 125 | 1 | −0.4 | 4.3 | 31 | n.d. | | | | |
| 30 | AP | 150 | 1 | −1.2 | 6.3 | 47 | Rh <3 ppm | | | | |
| 31 | AP | 150 | 1 | −1.4 | 8.6 | 59 | Ru 5 ppm | | | | |
| 32 | AP | 125 | 1 | −0.3 | 6.3 | 45 | n.d. | | | | |
| 33 | AP | 100 | 1 | −0.6 | 4.3 | 36 | n.d. | | | | |
| 34 | AP | 150 | 1 | 0.4 | 6.4 | 49 | n.d. | | | | |
| 35 | AP | 150 | 1 | 1.2 | 2.5 | 21 | n.d. | | | | |

AP: atmospheric pressure
n.d.: not determined

We claim:

1. A process for the preparation of alkanolamines having improved color quality by treating the alkanolamine with hydrogen in the presence of a hydrogenation catalyst at elevated temperature, which comprises using, as hydrogenation catalyst, a heterogeneous catalyst comprising Re, Ru, Rh, Pd, Os, Ir, Pt and/or Ag and a support material chosen from the group consisting of activated carbon, alpha-aluminum oxide, zirconium dioxide and titanium dioxide, where the catalyst, in the case of activated carbon as support material, has a cutting hardness of at least 10 N, a side crushing strength of at least 30 N or a compressive strength of at least 25 N.

2. A process as claimed in claim 1, which comprises using a hydrogenation catalyst comprising Ru, Rh, Pd and/or Pt and a support material chosen from the group consisting of activated carbon and alpha-aluminum oxide, where the catalyst, in the case of activated carbon as support material, has a cutting hardness of at least 20 N, a side crushing strength of at least 50 N or a compressive strength of at least 40 N.

3. A process as claimed in claim 1, wherein the catalyst, in the case of activated carbon as support material, has a cutting hardness of at least 30 N, a side crushing strength of at least 80 N or a compressive strength of at least 60 N.

4. A process as claimed in claim 1, wherein the catalyst, in the case of activated carbon as support material, has a surface area of from 500 to 2000 m²/g and a pore volume of from 0.05 to 1.0 cm³/g.

5. A process as claimed in claim 1, wherein the catalytically active mass of the catalyst comprises from 50 to 99.95% by weight of the support material and from 0.05 to 50% by weight of the noble metal, calculated as metal in oxidation state 0.

6. A process as claimed in claim 1, wherein the catalytically active mass of the catalyst comprises from 70 to 99.95% by weight of the support material and from 0.05 to 30% by weight of the noble metal, calculated as metal in oxidation state 0.

7. A process as claimed in claim 1, wherein the catalytically active mass of the catalyst consists of from 80 to 99.95% by weight of the support material and from 0.05 to 20% by weight of the noble metal, calculated as metal in oxidation state 0.

8. A process as claimed in claim 1, wherein the treatment is carried out at a superatmospheric pressure of from 0 to 50 bar.

9. A process as claimed in claim 1, wherein the treatment is carried out at a temperature of from 70 to 160° C.

10. A process as claimed in claim 1, wherein the alkanolamine used is ethanolamine or propanolamine.

11. A process as claimed in claim 1, wherein the alkanolamine used is triethanolamine or aminoethylethanolamine.

12. A process as claimed in claim 1, wherein the prepared alkanolamine, during storage for four months in a sealed container with the exclusion of light at temperatures of from 10 to 30° C., has, following acid treatment, an APHA color number (DIN-ISO 6271) of from 0 to 100 and an absolute value for the numerical measure a* according to the CIE-Lab system of from 0 to 3.5.

13. A process as claimed in claim 1, wherein the prepared alkanolamine has from 0.1 to 30 ppm (parts by weight) of impurities which originate from the hydrogenation catalyst.

* * * * *